United States Patent [19]

St. Remy et al.

[11] Patent Number: 4,740,371
[45] Date of Patent: Apr. 26, 1988

[54] TREATMENT OF ALLERGY

[75] Inventors: Jean-Marie St. Remy, Grez-Doiceau; Philippe Lebrun, Namur; Serge Lebecque; Pierre Masson, both of Brussels, all of Belgium

[73] Assignee: International Institute of Cellular and Molecular Pathology, Brussels, Belgium

[21] Appl. No.: 651,073

[22] Filed: Sep. 17, 1984

[51] Int. Cl.$^4$ .................... A61K 39/395; A61K 39/35
[52] U.S. Cl. ........................................ 424/85; 424/88; 424/91; 530/389; 530/390; 530/391; 514/826; 514/829; 514/890
[58] Field of Search ............................ 424/85, 88, 91; 514/826, 829, 890; 260/112 R, 112 B

[56] References Cited

U.S. PATENT DOCUMENTS

| | | | |
|---|---|---|---|
| 4,140,679 | 2/1979 | Malley | 424/88 |
| 4,234,569 | 11/1980 | Marsh | 424/91 |
| 4,344,938 | 8/1982 | Sedlacek et al. | 260/112 B |
| 4,545,986 | 10/1985 | Malley | 424/91 |
| 4,564,600 | 1/1986 | Ali et al. | 436/513 |

FOREIGN PATENT DOCUMENTS 0209229 12/1982 Japan ..................................... 424/88

OTHER PUBLICATIONS

Arend et al, "In Vitro Adherence of Soluble Immune Complexes to Macrophages", 136, J. Exp. Med., 514 (1972).
Klaus, "Cooperation Between Antigen-Reactive T Cells and Anti-Idiotypic B Cells in the Anti-Idiotypic Response . . . ", 278, Nature, 354 (Mar. 22, 1979).
Klaus, "Generation of Memory Cells. III. Antibody Class Requirements for the Generation of B-Memory Cells by Antigen-Antibody . . . ", 37, Immunology, 345 (1979).
Caulfield et al, "Induction of Idiotype-Specific Suppressor T Cell with Antigen/Antibody Complexes", 157, J. Exp. Med., 1713 (1983).
Blaser et al, "Immune Networks in Immediate Type Allergic Diseases", 418, Ann. NY Acad. Sci., 330 (1983).
Blaser et al, "Regulation of the IgE Antibody Response by Idiotype-Anti-Idiotype Network", 32, Prog. Allergy, 203 (1982).
Blaser et al, "Regulatory Effects of Isologous Anti-Idiotypic Antibodies on the Formation of . . . ", 14, Eur. J. Immunol., 93–98 (1984), 50, Fed. Reg., 3082 (Jan. 23, 1985).

Primary Examiner—John Kight
Assistant Examiner—Garnette D. Draper
Attorney, Agent, or Firm—Lane & Aitken

[57] ABSTRACT

In the treatment of allergy, desensitization is effected by administering the allergen in admixture with an antibody thereto, the antibody being present in a molar excess. The antibody is preferably one raised in the patient.

18 Claims, No Drawings

TREATMENT OF ALLERGY

BACKGROUND OF THE INVENTION

This invention relates to a method of treating allergy, particularly immediate hypersensitivity, and to pharmaceutical compositions useful therefor.

Immediate hypersensitivity (or anaphylactic response) is a form of allergic reaction which develops very quickly, i.e. within seconds or minutes of exposure of the patient to the causative allergen, and it is mediated by IgE antibodies made by B lymphocytes. In non-allergic patients, there is very little IgE but, in a person suffering allergy, the concentration of IgE is very much higher. This elevated amount of IgE mediates immediate hypersensitivity by priming mast cells which are abundant in the skin, lymphoid organs, in the membranes of the eye, nose and mouth, and in the respiratory tree and intestines. Mast cells have surface IgE receptors, and the elevated concentrations of IgE in allergy-suffering patients become bound to them. When this bound IgE is subsequently contacted by the appropriate allergen, the mast cell is caused to degranulate and release various substances such as histamine into the surrounding tissue. It is the release of these substances which is responsible for the clinical symptoms typical of immediate hypersensitivity, namely contraction of smooth muscle in the airways or the intestine, the dilation of small blood vessels and the increase in their permeability to water and plasma proteins, the secretion of thick sticky mucus, and (in the skin) the stimulation of nerve endings that results in itching or pain.

Immediate hypersensitivity is, at best, a nuisance to the sufferer: at worst it can present very serious problems and can in rare extreme cases even result in death. Efforts have been made for many years past to find some way of effectively treating sufferers, and essentially three such ways have been found. These are: avoidance of allergen, desensitization, and the use of drugs. Of these, avoidance of the allergen is in one sense clearly the best approach but, of course, it is in practice very difficult, and usually impossible, to achieve. Treatment by the use of drugs is useful, but it is, in the main, directed to alleviating the symptoms of allergy rather than dealing with its causes. Also, there are disadvantages in the use of certain drugs, and it is by no means always possible using drugs to assist patients as much as could be desired.

The third method of treatment, namely desensitization, has long been recognised as perhaps the most hopeful practical approach to the problem. It has been known for over 60 years that the injection into a patient of initially small, but subsequently increasing, amounts of the offending allergen itself, over a period of time, can often result in an improved resistance to that allergen, i.e. a reduced tendency to develop immediate hypersensitivity upon normal exposure to the allergen. This procedure is known as desensitization (or "allergen immunotherapy"). Whilst it is not useful in the treatment of food allergies, it is useful in the treatment of, for example, inhalant allergen-derived sensitivity and allergic reactions due to insect stings.

Curiously, although desensitization has been successfully practiced for many years past, the mechanism by which it works is still not known. In most patients, the injection of the allergen appears to give rise, not to IgE antibodies, but rather to IgG antibodies which (upon inhalation by the patient of the allergen in question) combine with the allergen to block its ability to bind to the mast cell IgE. These IgG antibodies are called "blocking antibodies". However, this hypothesis does not always fit the facts. In some patients who are successfully desensitized, there is little specific IgG in their blood, and in other patients in whom the injections have apparently been ineffective against allergy, there is a large amount of the particular IgG.

Whatever the mechanism may be, it remains the fact that many (though not all) sufferers of immediate hypersensitivity can be helped considerably by desensitization. The technique involves injecting the allergen (to which the patient has become sensitized) into the patient over a relatively long period of time, e.g. one year or more. Initially, the doses used are very small but, in the absence of contra-indications, they are increased rapidly to high levels which are necessary if the treatment is to be effective. There are certain problems in desensitization treatment. Firstly, it is necessary for the patient to have injections very frequently, e.g. initially every two or three days, gradually reducing to, say, once every two or three weeks. This is not only a time-consuming procedure, but is also disruptive of the patient's normal routine, and generally undesirable. Also, the dose of allergen administered has to be carefully monitored and controlled, which adds to the complexity of the procedure. A second problem is that, in the treatment itself, there is an element of risk to the patient. Whilst, as we have said, initial doses of the allergen are very small, and precautions are routinely taken to watch for any allergic response, nevertheless local or systemic allergic reactions (such as hives, asthma and faint) do sometimes occur and can, in exceptional cases, even cause death. For these and other reasons, many practicing physicians are skeptical of desensitization techniques.

Attempts have been made in the past to overcome or avoid these problems. To reduce the frequency of injection, preparations have been administered which release the allergen slowly over a period of time. These have not been very successful for a number of reasons, an important one of which being that, once administered, no control can be exercised over the amount of allergen released into the patient's blood. Another way in which the frequency of injection might be reduced would be to devise a treatment whereby the necessary large doses of allergen could be administered rather sooner to the patient, but to date there has been no such treatment devised. Attention has also been directed in the past to the possibility of administering modified allergens instead of the "pure" material itself. Thus attempts have been made to modify an allergen chemically so that, whilst its immunogenicity (i.e. its ability to cause an immune response in the patient), is unchanged, its allergenicity is substantially reduced. Some limited success has been achieved with this approach, but it has certain disadvantages of its own. Firstly, each allergen (and there are of course a vast number of allergens against which patients can become sensitized and thus need desensitization treatment) has to be modified individually in accordance with its particular chemical structure: thus, there is no satisfactory universally applicable technique for modifying allergens for a desensitization treatment. Secondly, a very considerable amount of work can be involved in devising an acceptable modified allergen, bearing in mind the requirements for it to be useful in the desensitization treatment, including the necessity for the chemical modification not itself to cause any adverse reaction in the patient. Thirdly, because accurate control of dose is so important in a desensitization treatment (where an accidental overdose could kill) there can be problems with modified allergens in determining the proper dose required.

Further background information on allergy and desensitization treatments may be found in Buisseret, Paul D., "Allergy," Scientific American, August 1982, pp. 82–91; Sanders, Howard J., "Allergy: A protective mechanism out of control," vol. 48, pp. 84–134 (1970); and "Primer on Allergic and Immunologic Disease," JAMA, volume 248, no. 20 Nov. 26, 1982).

SUMMARY OF THE INVENTION

We have now found a way of carrying out the desensitization treatment for immediate hypersensitivity by which many of the problems and disadvantages of prior known procedures are reduced or even overcome. In particular, we have found a way of administering allergens which is universally applicable to all allergens, which does not expose the patient to any increased risk and by which large doses of allergen can be administered.

In accordance with the present invention, patients (being human or animal) who have immediate sensitivity to an allergen are desensitized by administering to them the said allergen in admixture with antibody directed against the allergen.

The invention further provides a pharmaceutical composition for use in the above method, which composition comprises a mixture of an allergen and antibody thereto, in a suitable form for administration, preferably in a sterile injectable form.

It is to be understood that, in the context of the present invention, the term "allergen" means a specific subclass of antigen which can trigger immediate hypersensitivity (anaphylactic response) which is mediated by IgE antibody.

DESCRIPTION OF THE PREFERRED EMBODIMENT

We have found that, by mixing the allergen with an antibody thereto, a number of advantages are achieved over prior art procedure. Firstly, this is a universally applicable and relatively very simple way of treating an immediate hypersensitivity. Antibody can be raised to any and every allergen, and the mere admixture thereof with the allergen is a straightforward procedure. Secondly, since (as is described in more detail hereafter), the antibody can be derived from the patient himself, the risk of any adverse reaction thereto is virtually eliminated. This is in sharp contrast to prior art procedures for chemically modifying allergens, where adverse reactions can be obtained. Indeed, where an allergen is modified by coupling it chemically to another material, the patient can become sensitized to this other material. This does not occur with the use of naturally occurring antibody. Thirdly, pure allergen can be used and the dose of allergen can be very closely and simply controlled. Furthermore, the clinical efficacy of the treatment is very good. Patients who have failed to respond to prior art desensitization techniques have been found to benefit from the method of the present invention. Furthermore, we have found that the duration of treatment of the present invention can be markedly less than in prior known procedures, which may be because it is usually possible in accordance with the present invention to reach much higher allergen doses more quickly than in prior known procedures. Also, the treatment of the invention does not appear to generate any significant local or systemic allergic reaction, and thus the risks in its use are less than those using the prior art modified allergens.

We do not know the mechanism by which the treatment method of the invention works. Whilst we do not wish to be bound by this hypothesis, we believe that the mixture of allergen and antibody will inevitably contain allergen: antibody immune complex, and that the antibody thus masks the allergenicity of the allergen. This would explain the observed very much reduced allergenicity of the complex. The reason why the method of the invention can achieve such a marked desensitization is not understood, and indeed any such explanation may have to wait upon a better understanding, by those skilled in the art, of the mechanism of desensitization generally. It is surprising that mixtures of allergens and antibodies thereto are so effective as desensitizing agents, in that there is no apparent reason why they should be.

It is not uncommon for patients who suffer anaphylactic response to a particular allergen, also to suffer such a response to one or more other allergens. However, it is possible by the method of the invention to desensitize such a patient in respect of two or more allergens simultaneously, by administering the said allergens in admixture with antibodies against each allergen. Thus, for example, a composition of the invention could comprise a mixture of two allergens and two antibodies (one directed against each allergen, respectively). Alternatively, simultaneous desensitization in respect of two or more allergens can be effected by administering two or more compositions of the invention, each composition comprising one allergen only and its respective antibody.

We have referred above to the composition of the invention comprising antibody against the allergen. It should be understood that, instead of whole antibody, antibody fragment such as $F(ab')_2$ can be used instead. Also, if desired, monoclonal antibodies can be used although we are not aware of any particular advantage in so doing.

In practicing the present invention, there are essentially three steps, namely:
(1) identification of the allergen and preparation of the antibody thereto;
(2) formation of the mixture of allergen and antibody to make a composition of the invention; and
(3) administration of the composition to the patient.
These steps will now be described in more detail.

1. Preparation of the antibody

The allergen responsible for an allergy can be determined by standard known techniques. An antibody thereto is then generated. Three sources of antibody can be used:
(a) immunized animals, (b) individual blood donors and pooled plasma from multiple donors, and (c) the patient himself. We prefer to use antibodies from the patient because the patient will normally have larger amounts of the specific antibodies required than will blood donors. Antibodies of animal origin are generally the least desirable to use because of the risk of undesirable side-reactions.

The antibody can be polyclonal or monoclonal, and can be used either in the form of, for example, unfractionated plasma or serum, or as an immunoglobulin fraction or in a purified form. The use of polyclonal antibodies decreases the risk of allergic reactions against unmasked antigenic determinants. Purification of the antibody has the advantage of removing therapeutically irrelevant materials. The antibody can be purified by various known techniques such as, for example, by specific absorption on the allergen which has been insolubilized by coupling to a solid phase. The antibody can then be recovered by elution under conditions which dissociate the antigen-antibody complex, such as conditions of extreme pH or by the use of chaotropic agents.

2. Formation of the composition of the invention

Compositions of the invention are made by mixing the allergen (or allergens) with the antibody (or antibodies), in a form suited to the particular administration route to be adopted. Because the antibody will react only with its specific antigen (allergen), almost any preparation of allergen, even very crude, can be used provided it is devoid of toxic substances. However, the use of pure or relatively pure preparations of allergen is preferred because it is then easier to assess and control the amount of allergen present, which is important in controlling doses.

The proportion of antibody to be added to the allergen is defined essentially by the neutralizing power of the antibody. Enough antibody must be used so that, when the composition is administered, there is practically no allergic effect by the allergen. This minimum will normally be a molar excess of antibody of at least about 3. If desired, routine testing will reveal, with any particular allergen and antibody, the minimum amount of antibody to be used. There is no maximum to the amount of antibody which may be used. For safety, we use a molar excess of up to about 500. An even larger antibody excess can be utilized but it is, of course, wasteful of the valuable material. One simple method of preparing the mixture of allergen and antibody, which method avoids the necessity of purifying the allergen or the antibody, is to use the immune precipitate. This can be prepared by incubating the patient's plasma or serum with the allergen, and then centrifuging. The precipitation process can be enhanced by addition of polymers such as polyethylene glycol and dextran, or biological reagents such as rheumatoid factor or the $C1_q$ factor of complement. These techniques are well known.

The compositions of the invention may contain, in addition to the allergen and antibody, any other suitable components. For example, in the case of injectables, they may contain human albumin to prevent denaturation of antibody, antiseptic agents (e.g. phenol), and adjuvants (e.g. peptidoglycans, tyrosine crystals).

The liquid carrier for injectables may be, for example, distilled water, or more preferably saline (9 g/l sodium chloride) or buffered saline (pH 7.0). In general, any liquid carrier should be of low irritance, e.g. of neutral pH and physiological ionic strength.

The strength of the compositions is preferably expressed in terms of allergen concentration and allergen/antibody ratio. In general, the antibody will be present in a molar excess of at least 3, and most usually in a molar excess of up to about 500.

The compositions of the invention may (as described above) be in a variety of forms depending on the administration route. Thus, they may for example be in sterile injectable form. Alternatively, they may be in a form suitable for local applications on nasal, bronchial, lacrimal and gastrointestinal mucosae, in which case they will be in a form similar to eye or nasal drops, or in aerosol form, or as protected enteric capsules or the like.

In the case of liquids, these may be solutions or suspensions. The liquids may be stored in ampoules or they may be lyophilized and reconstituted immediately prior to use. The compositions of the invention are fairly stable and, in sterile ampoules, can normally be stored at room temperature for at least 4 to 5 weeks, or at 4° C. for at least 12 to 24 months. When frozen or lyophilized, their storage life is much longer.

3. Administration of the compositions

The injectable compositions of the invention can be injected by various routes: intradermal, subcutaneous, intramuscular and (but only with great care) intravenous. We prefer the intradermal route, which has the advantage of causing a very clear skin reaction if insufficient antibody is present to provide the necessary neutralizing of the allergen in the composition. The frequency of injections can vary very widely, for example from daily to yearly, depending upon the type of allergen, the severity of the disease and the stage of desensitization. The dose of allergen is usually doubled at each injection, which is, of course, a very fast increase in dose. Greater or lesser increases can of course be used depending upon the clinical situation.

Those compositions of the invention other than injectables will be administered as suitable. For example, respiratory allergy can be treated by aerosol administration using, for example, a Micronebulizer (Bird) to give particles between 0.5 and 5 μm at a rate of 0.35 ml/min, the patient being instructed to breath in once deeply and to hold their breath for two seconds. The dose can be repeated at, for example, weekly intervals over the desired period.

The quantities of allergen in the composition used for the first administration, e.g. injection, can be equal to or usually much higher than (80-fold) those amounts of allergen used in classical desensitization techniques. Thus, in classical techniques, the usual initial dose is from about $10^{-10}$ g to $10^{-9}$ g: for example, from 0.1 to 1 nanogram of purified allergen from the house dust mite can be used for the first injection in classical desensitization techniques. In the method of the present invention, the initial dose of allergen is used with a molar excess of from 3 to 500 of antibody (i.e. an antibody:allergen molar ratio of 3 to 500). The preferred initial dose, in accordance with the invention, will normally be different from one patient to another and will correspond to that dose which causes a skin reaction of 3 to 5 mm diameter after intradermal injection.

In order that the invention may be more fully understood, the following Example is given which describes, by way of illustration only, the treatment of three patients suffering from allergic asthma caused by house dust mites, *Dermatophagoides pteronyssinus* (DPT).

EXAMPLE

1. Patients

The three patients are identified as follows:

| Patients | Initials | Sex | Age |
|---|---|---|---|
| 1 | L. L. | F | 40 |
| 2 | B. J. | M | 21 |
| 3 | W. E. | F | 37 |

They were selected on the following criteria:

1. Long-term (more than 5 years) history of invalidating bronchial asthma, keeping them away from work at least 3 months a year and having necessitated at least one admission in intensive care units.
2. Evidence for an extrinsic asthma where DPT was clearly the causative agent.
3. High sensitivity to DPT shown by intradermal testing and bronchial provocation test with the allergen.
4. High level of DPT-specific antibodies.
5. A history of at least one unsuccessful classical desensitization to DPT.
6. No permanent corticotherapy.

All three patients were taking drugs daily. These included theophylline and derivatives, $\beta_2$-agonists in aerosol, and topical nasal beclomethasone in one patient (B.J.). They were not suffering from any other known disease, except that two of them (B.J. and W.E.) had a chronic rhinitis. One patient (W.E.) was also highly sensitive to grass pollen as shown by hay fever and asthma during the pollen season and by a high level of specific IgE antibodies against pollens.

They were submitted to a 3-month treatment in accordance with the invention, using antigen-antibody complexes made with their own purified antibodies.

2. Antibody purification a. Plasma collection and handling

One hundred ml of plasma from each patient were precipitated with 18% $Na_2SO_4$ at 37° C. for 4 hours. The precipitate was washed and resuspended in phosphate buffered saline (PBS) containing 1M NaCl and, after centrifugation to clear off small particles, filtered through a 0.45μ filter. Twenty-five ml of this solution were applied onto a 9×90 cm TSK HF-55 (Merck, Darmstadt) gel column, chromatographed at a rate of 250 ml/h and recovered in 10 ml fractions. The two main peaks represented IgM and IgG (plus IgA and IgE). Cross contamination was about 5% as shown by immunodiffusion.

IgM and IgG (plus IgA and IgE) were concentrated separately by ultrafiltration through a XM-100 Amicon membrane to a volume of ~25 ml and dialyzed for 3 days against PBS with several changes of the dialysis bath. The solutions were than passed through a 0.22 μGV filter (Millipore) and stored in sterile conditions.

b. Preparation of the immunoadsorbent

Commercially available allergens were purified by gel filtration chromatography on Ultrogel AcA 44 and/or Ultrogel AcA 54 (LKB) and, in some cases, by specific immunoadsorption on insolubilized polyclonal or monoclonal specific antibodies.

The allergen was then coupled with carbodiimide to carboxylated agarose (CH-Sepharose 4B; Pharmacia Fine Chemicals). For this purpose, the allergen was incubated at pH 4.5 with 0.1M carbodiimide and carboxylated agarose for 24 hr. at 21° C.

The remaining reactive groups on the solid phase were inactivated by its incubation with 1M glycine for 3 h. at 21° C. The immunoadsorbent was then washed alternatively with 0.1M acetate buffer pH 4.0 and 0.1M carbonate buffer pH 8.3, both containing 0.5M NaCl. To avoid the elution of undesired material with the antibodies of interest, we submitted the gel prior to immunoadsorption to the elution conditions to be described hereafter and to an additional washing with 3M ammonium thiocyanate.

c. Extraction of the specific antibodies

The immunoglobulin fractions (1–2 g) from each of the patients were applied onto an immunoadsorbent column (5 ml; 10×2 cm; flow rate 20 ml/h) and the specific antibodies recovered after appropriate washings.

1. Wash with PBS until the optical density at 280 nm is less than 0.02.
2. Wash with PBS containing 1M NaCl to eliminate non-specific adsorption.
3. Wash with 50 ml of 9 g/l NaCl.
4. Elution is made with successive aliquots of 50 mM citric acid, pH 2.7 followed by PBS.

Each new wash and elution step was pursued until no protein was detectable in the effluent. Fractions eluted with citric acid and PBS were pooled immediately, neutralized with dropwise addition of 2M TRIS-HCl buffer, concentrated on a YM 10 ultrafiltration membrane and dialyzed against PBS for 48 h. The eluate was then filtered through a 0.22μ filter and stored at 4° C. in sterile vials. The immunoadsorbent was washed with 3M ammonium thiocyanate for 20 min and finally with 100 ml PBS. All buffers were filtered in 0.22μ filter.

d. Yield and class repartition of specific antibodies

The amounts of specific antibodies, estimated by optical absorbance at 280 nm ranged from 2 to 6 mg per 100 ml of plasma.

The analysis of the eluted antibodies failed to reveal the presence of autoantibodies such as rheumatoid factor (anti-IgG autoantibody) and showed that the specific antibodies were of the following classes: IgG (50%), IgM (35%), IgA (14.5%) and IgE (0.5%). No other plasma protein was detected in significant amounts by immunonephelometry.

3. Preparation of antigen-antibody complexes a. Precipitation curve

To determine the optimal ratio of antigen vs. antibody in the complexes at which most antigenic determinants are hidden by specific antibodies, we made a precipitation curve as follows. Into a series of tubes containing the same amounts of antibodies were pipetted increasing dilutions of antigen in 0.1M borate buffer pH 8.5. Polyethylene glycol was then added to a final concentration of 200 gll. After incubation for 4 h. at 21° C. then for 16 h. at 4° C. and centrifugation at 8,000 g for 20 min., the precipitates were washed and the amount of protein in the supernatant and the precipitate estimated by the Lowry technique. For safety purposes, we used for the injection 1/5 of the amount of antigen giving the largest precipitate. In these conditions, the antibody was in large excess (antigen/antibody weight ratio = 1/500).

b. Preparation of the complexes and injectable compositions

Antigen and antibody were mixed in a weight ratio of 1/500 in 9 g/l NaCl containing 0.3% human serum albumin and 4% phenol. All solutions were passed through a sterile 0.22μ filter and handled in sterile conditions. The final volume was 2 ml and contained 400 μg antibody and 800 ng antigen. The injectable solutions were kept in sealed vials at 4° C. until use.

4. Injections a. Patients' tolerance

To assess the patients' tolerance to the compositions, we serially diluted the antigen in the presence of a constant amount of antibodies (the compositions being generally as described in paragraph 3(b) above). Each of these dilutions was then injected intradermally in 20 μl aliquots starting with the lowest antigen-antibody ratio.

An interval of 15 minutes was allowed between the injections. The highest antigen-antibody ratio giving an acceptable skin reaction (wheal of maximum 3 cm diameter) was chosen and used throughout the study. At a ratio of 1/500 the complex usually caused a small skin reaction or none at all.

b. Injection scheme

Intradermal injections on the internal side of the arm were repeated every week for six weeks, then every fortnight for a total of three months. In a typical scheme, a volume of 20 μl containing 4 μg antibody and 8 ng antigen was used for the first injection. This volume was doubled every week up to a maximum of 200 μl and maintained to the end of the study (a total of 3 months).

5. Clinical outcome a. Subjective assessment

No side effects were noted. The patients were reported to feel well and improved as far as their asthmatic symptoms were concerned. No one injection in any of the three patients gave a clear allergic reaction (there were 40 injections in all). At the injection site, there was either a relatively weak skin reaction or none at all.

b. Clinical assessment

Three criteria were used to evaluate the clinical outcome of the patients:
skin reactivity to the allergen
bronchial provocation test with the allergen
baseline lung function 1. Skin reactivity The allergen was serially diluted in 9 g/l NaCl with 0.3% albumin and 4% phenol, and 20 μl was injected intradermally into the arm. After 20 minutes, the wheal area was measured by planimetry and plotted on a graph against the allergen concentration. The amount of allergen needed to obtain a certain wheal area was then read on the curve. The same preparation of allergen was used for the tests made before and after immunotherapy. In the three patients, after treatment it was found necessary to use 16 times more allergen to induce a skin reaction as intense as the one observed before treatment.

2. Bronchial provocation test

To assess the bronchial reactivity to DPT before and after immunotherapy, we submitted the patients to aerosols of DPT at different dilutions. Under well standardized conditions, the forced expiratory volume per second ($FEV_1$) and airway conductance were assessed. By plotting the values of these two parameters against the allergen dilution we determined the dilution of allergen giving a 20% fall in $FEV_1$ or a 35% decrease in airway conductance. Non-specific bronchial reaction to acetylcholine was assessed in this way. The following Table compares the bronchial sensitivity of our patients before and after three months of immunotherapy.

TABLE

| Patients | Non-specific bronchial reactivity to acetyl-choline (dilutions) | | Specific bronchial Reactivity to DPT (dilutions) | |
| --- | --- | --- | --- | --- |
| | Before | After | Before | After |
| 1 (L. L.) | $10^{-3}$ | ND* | $10^{-3.8}$ | ND |
| 2 (B. J.) | $10^{-2.5}$ | $>10^{-2}$** | $10^{-2.6}$ | $>10^{-1}$** |
| 3 (W. E.) | $10^{-3}$ | $10^{-3.5}$ | $10^{-4}$ | $>10^{-1}$** |

*ND = not done.
**No bronchial reactivity observed at the highest concentration of acetylcholine or DPT used.

3. Baseline lung function

Baseline $FEV_1$ and airway resistance were assessed during the clinical follow-up. The three patients were up to 100% of the normal values (111, 127 and 102% respectively for patients 1, 2 and 3) after three to four weeks of treatment. These values were maintained throughout the study except for patient 1 where the $FEV_1$ dropped to 70% of the normal; for this reason no bronchial provocation test was done in this patient.

6. Laboratory investigations a. Specific antibodies

| Patients | DPT specific antibodies | | | | Total IgE** | |
| --- | --- | --- | --- | --- | --- | --- |
| | IgG* | | IgE** | | | |
| | Before | After | Before | After | Before | After |
| 1 (L. L.) | 31 | 45 | 16 | 124 | 1,696 | 1,470 |
| 2 (B. J.) | 31 | 34 | 118 | 288 | 2,182 | 2,058 |
| 3 (W. E.) | 27 | 32 | 10 | 42 | 855 | 551 |

*in μg/ml
**in ng/ml

Laboratory investigations where made before and after 9 weeks of treatment. Results are given in the above table. It can be seen that:

a. DPT specific IgG increases moderately.
b. DPT specific IgE increases dramatically.
c. Total IgE tend to decrease slightly.

The same profile was observed for the three patients.

b. IgE synthesis in vitro

The total amount of IgE synthesis in vitro was evaluated on peripheral lymphocytes maintained in culture for 7 days. IgE was assayed in the supernatant by radioimmunoassay. Results are as follows:

| Patients | WEEKS | | | | | |
| --- | --- | --- | --- | --- | --- | --- |
| | 1 | 3 | 7 | 11 | 15 | 18 |
| 1 (L. L.) | 1,300* | 850 | 395 | 1,500 | 380 | 7,400 |
| 2 (B. J.) | 1,600 | 810 | 400 | 200 | ND | <50 |
| 3 (W. E.) | 6,250 | 4,500 | 300 | 350 | ND | <50 |

*in pg/ml supernatant.
ND means "not determined".

Results indicated in the Table above show that in vitro production of total IgE tends to decrease in all three patients through the seventh week of the study. These results continue in Patients 2 and 3 through the 18th week. Total IgE levels, however, can be influenced by several factors. During the course of the study it was determined that Patient 1 had developed an infectious bronchitis which may account for the increase in the total IgE count.

In conclusion, three patients who had severe asthma which was resistant to classical immunotherapy were clearly improved after the repeated injections of allergen-antibody mixtures (in accordance with the invention), as shown mainly by the higher resistance to intradermal or intrabronchial challenges with DPT.

We claim:

1. A pharmaceutical composition for administration to human beings for the treatment of immediate hypersensitivity against an allergen, said composition consisting essentially of:
an immune complex of the allergen and a purified human-derived antibody specific thereto, said allergen being selected from a specific subclass of antigen that can trigger immediate hypersensitivity that is mediated by IgE antibody and said antibody being present in a molar excess, with respect to the allergen, of at least about 3 to about 500; and a physiologically acceptable carrier or diluent of approximately neutral pH.

2. A composition according to claim 1, wherein the amount of antibody is such that, when the composition is administered, there is no significant allergic effect by the allergen.

3. A composition according to claim 1, wherein said carrier is a liquid and said composition is in sterile injectable form.

4. A composition according to claim 3, wherein the liquid is saline.

5. A composition according to claim 1, which is in the form of an aerosol, enteric capsules or viscous liquid to be administered in the form of drops to nasal, bronchial, lacrimal or gastrointestinal mucosae.

6. A composition according to claim 1, for administration to a patient suffering immediated hypersensitivity to the allergen, wherein the said antibody has been derived from the patient.

7. A composition according to claim 1, which comprises two or more allergens and antibodies thereto.

8. A composition according to claim 1, in lyophilized form.

9. A composition according to claim 1, wherein said allergen is present in a range of from about $10^{-10}$ g. to $10^{-9}$ g.

10. A composition according to claim 1, wherein said antibody is an F(ab')$_2$ antibody fragment.

11. A method of reducing the immediate hypersensitivity of an animal to an allergen, wherein the animal is subjected to a desensitization treatment in which the allergen is repeatedly administered to the animal, comprising the step of administering the allergen in admixture with antibody specific thereto.

12. A method of administering an allergen to an animal which has an immediate hypersensitivity thereto, which comprises first mixing the allergen with an antibody specific thereto, and then administering the mixture to the animal.

13. A method according to claim 11, wherein the amount of antibody is such that, when the composition is administered, there is no significant allergic effect by the allergen.

14. A method according to claim 11, wherein the molar amount of antibody is at least three times the molar amount of allergen.

15. A method according to claim 11, further comprising the step of deriving the antibody from the animal.

16. A method according to claim 11, wherein said step of administering comprises injecting a mixture of allergen and antibody.

17. A method according to claim 11, wherein said step of administering comprises administering a mixture of said allergen and antibody in the form of an aerosol, enteric capsule or drops of a viscous liquid.

18. A method according to claim 11, wherein said animal is human and said method further comprises the step of deriving said antibody from human serum.

* * * * *